United States Patent [19]
Ku et al.

[11] Patent Number: 5,892,008
[45] Date of Patent: Apr. 6, 1999

[54] PROCESS FOR THE PREPARATION OF 6-O-METHYL ERYTHROMYCIN A USING 9-HYDROXY ERYTHROMYCIN DERIVATIVES

[75] Inventors: Yi-Yin Ku, Buffalo, Ill.; David A. Riley, Kenosha, Wis.; Elaine C. Lee, Wheeling; Jien-Heh Tien, Libertyvill, both of Ill.

[73] Assignee: Abbott Laboratories, Abbott Park, Ill.

[21] Appl. No.: 991,648

[22] Filed: Dec. 16, 1997

[51] Int. Cl.$^6$ .............................. C07H 1/00; C07H 17/08
[52] U.S. Cl. ............................................ 536/18.5; 536/7.2
[58] Field of Search ..................... 536/18.5, 7.2

[56] References Cited

U.S. PATENT DOCUMENTS 4,331,803  5/1982  Watanabe et al. .

FOREIGN PATENT DOCUMENTS 0180415  5/1986  European Pat. Off. .
0195960  10/1986  European Pat. Off. .
0272110  6/1988  European Pat. Off. .

*Primary Examiner*—Gary L. Kunz
*Attorney, Agent, or Firm*—Portia Chen; Mona Anand

[57] ABSTRACT

The claimed invention provides a novel method of preparing 6-O-methyl erythromycin A. The process comprises the steps of reducing the 9-keto group of erythromycin A to form a 9-hydroxy erythromycin A, protecting the 9-, 2'-, and/or 4"-hydroxyl groups of erythromycin A, selectively methylating the 6-position of the 9-hydroxy erythromycin A derivative, deprotecting the hydroxyl groups and oxidizing the 9-hydroxyl to afford 6-O-methyl erythromycin A.

14 Claims, No Drawings

PROCESS FOR THE PREPARATION OF 6-O-METHYL ERYTHROMYCIN A USING 9-HYDROXY ERYTHROMYCIN DERIVATIVES

TECHNICAL FIELD

The present invention relates to a novel process for the preparation of 6-O-methyl erythromycin A via 9-hydroxy erythromycin derivatives.

BACKGROUND OF THE INVENTION

6-O-methyl erythromycin A, of the formula below, is a potent macrolide useful as an antibiotic.

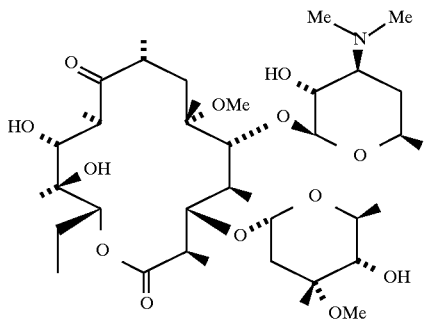

The process of synthesizing 6-O-methyl erythromycin A poses many significant challenges. In particular, the starting material, erythromycin A, is unstable and possesses many functional groups that require protection and deprotection during synthesis. Simple methylation of the 6-position of 2'- and 4"-protected erythromycin A derivatives commonly results in a mixture of methylation products. For this reason, it is difficult to develop an approach to 6-O-methyl erythromycin synthesis that allows for selective methylation at the 6-position and under reaction conditions that are compatible with the survival of erythromycin A.

At present, prior art methods approach this obstacle using a variety of different strategies. Known methods involve many steps of protecting and deprotecting various functional groups of the erythromycin A to achieve selective methylation at the desired 6-position. These strategies involve a multitude different intermediates, many of which are 9-oxime erythromycin A derivatives. Although oxime derivatives provide one useful alternative in the preparation of 6-O-methyl erythromycin, there remains a need for novel, effective methods of 6-O-methyl erythromycin A synthesis.

Previously developed methods attempt to achieve 6-O-methyl erythromycin synthesis via the following methods.

European Patent No. 0 272 110 discloses a process for making 6-O-methyl erythromycin A via a bis-TMS, 9-cyclohexyl ketal oxime. The ketal reagent is used in the presence of formic acid and in acetonitrile to form a protected 9-oxime-erythromycin A derivative.

European Patent No. 0 180 415 discloses a process using 9-benzyl oxime derivatives to form the 6-O-methyl erythromycin product. A substituted aryl chloride reagent is used to protect the 9-oxime and removed with palladium catalyst and hydrogen after methylation of the 6-position.

U.S. Pat. No. 4,311,803 discloses preparation of 6-O-methyl erythromycin A involving protection of 2'-hydroxyl and 3'-dimethylamino groups. The process involves using benzyloxycarbonyl (cbz) for protection of the 2'-hydroxyl and 3'-dimethylamino groups. The 3'-dimethylamino group must be regenerated by reductive N-methylation after removal of the cbz protecting group.

European Patent No. 0 195 960 discloses a process of synthesis for 6-O-methyl erythromycin A requiring a quaternary salt. An aryl chloride reacts with a 9-oxime derivative to form a quaternary salt. The salt is subsequently eliminated after 6-O-methylation.

There continues to be a need to provide a rapid, efficient method of producing 6-O-methyl erythromycin compounds that uses mild, neutral synthetic conditions and to provide novel intermediates useful in the production of 6-O-methyl erythromycin derivatives.

SUMMARY OF THE INVENTION

The present invention relates to a process for the preparation of 6-O-methyl erythromycin A. In one embodiment, the process of the claimed invention comprises:

a.) protecting the 2'-hydroxyl group of erythromycin A to form a 2'-protected erythromycin A derivative;

b.) reducing the 9-keto group of the 2'-protected erythromycin A derivative to form a 9-hydroxy-2'-protected erythromycin A derivative;

c.) protecting 9-hydroxy 2'-protected erythromycin A to form a 9-protected 2'-protected erythromycin A derivative;

d.) methylating the 6-position of the 9-protected-2'-protected erythromycin A derivative to form a 9-protected-2'-protected 6-O-methyl erythromycin A derivative;

e.) deprotecting the 9-protected-2'-protected 6-O-methyl erythromycin A derivative to form a 9-hydroxy 6-O-methylated erythromycin A derivative; and f.) oxidizing the 9-hydroxy of the 9-hydroxy 6-O-methylated erythromycin A to form 6-O-methyl erythromycin A.

In another embodiment, the 4"-hydroxyl group is optionally protected to form a 2',4"-protected erythromycin A derivative which is treated in accordance with steps (b)–(f).

In another aspect, the present invention provides certain intermediates formed during a process of this invention. Such intermediates correspond to the structure below,

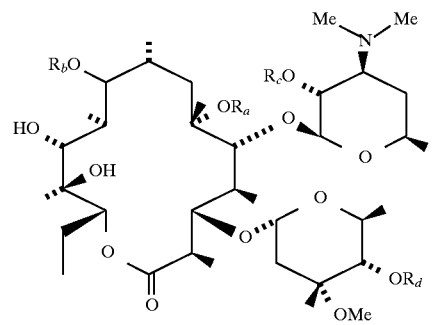

wherein $R_a$ is hydrogen or methyl; $R_b$, $R_c$, and $R_d$ are independently at each occurrence a hydrogen or a hydroxy protecting group, with the proviso that $R_b$ is not hydrogen when $R_a$ is methyl, and $R_c$ and $R_d$ are hydrogen. The hydroxy protecting groups are selected from the group consisting of the formula:

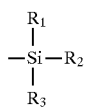

wherein $R_1$, $R_2$, and $R_3$ are at each occurrence triisopropyl, t-butyldimethyl, triethyl, isopropyldimethyl, t-butyldiphenyl, methyldiisopropyl, methyldi-t-butyl, tribenzyl, or triphenyl; $R_3Si$—X, where X is a halide including, chlorine, bromine, and iodine, p-toluenesulfonate or trifluoromethanesulfonate; —O—C(O)$_n$—R where n is 0, 1, 2, and R is an alkyl, substituted alkyl, alkoxy, substituted alkoxy, alkoxyalkyl, aryl, or substituted aryl; and $R_1R_2R_3SiOTf$, wherein $R_1$, $R_2$, and $R_3$ are as defined above.

DETAILED DESCRIPTION OF THE INVENTION

A number of defined terms are used herein to designate particular elements of the present invention. When so used, the following meanings are intended:

The term "alkyl" refers to saturated, straight or branched-chain hydrocarbon radicals containing between one and ten carbon atoms including, but not limited to, methyl, ethyl, propyl, isopropyl, n-butyl, tert-butyl and neopentyl. Preferably, alkyl is limited to 1–4 carbons.

The term "aryl" refers to an aromatic hydrocarbon of 1–6 carbons, as for example benzyl, diphenylbenzyl, trityl and phenylethyl.

The term "alkoxy" refers to a hydrocarbon radical which is joined to the rest of the molecule via an ether linkage (i.e., through an oxygen atom), as for example methoxy, ethoxy, butoxy, and the like.

The term "cycloalkyl" refers to a saturated monocyclic hydrocarbon radical having from three to eight carbon atoms in the ring and optionally substituted with between one and three additional radicals selected from among lower alkyl, halo(lower alkyl), loweralkoxy, and halogen. Examples of cycloalkyl radicals include, but are not limited to, cyclopropyl, cyclobutyl, cyclopentyl, cyclohexyl, cycloheptyl, 1-fluoro-cyclopropyl, and 2-fluorocyclopropyl.

The term "deprotecting reagent" refers to a reagent which reacts with a protecting group to remove the group used to protect hydroxy groups against undesirable reactions during synthesis of the desired final product. Examples of deprotecting agents include but are not limited to n-tetrabutylammonium fluoride, acetic acid/THF/water, citric acid/methanol, Dowex resin/methanol, potassium carbonate/methanol, n-tetrabutylammonium chloride/potassium fluoride, hydrogen fluoride/acetonitrile.

The term "hydroxy-protecting group" or "O-protecting group" as used herein refers to a substituent which protects hydroxyl functionalities against undesirable reactions during synthetic procedures such as those O-protecting groups disclosed in Greene, "Protective Groups in Organic Synthesis," (John Wiley & Sons, New York (1981)), which is incorporated herein by reference. O-protecting groups comprise substituted methyl ethers, for example, methoxymethyl, benzyloxymethyl, 2-methoxyethoxymethyl, 2-(trimethylsilyl)ethoxymethyl, t-butyl, benzyl, and triphenylmethyl; tetrahydropyranyl ethers; substituted ethyl ethers, for example, 2,2,2-trichloroethyl; silyl ethers, for example trimethylsilyl, t-butyldimethylsilyl and t-butyldiphenylsilyl; and esters prepared by reacting the hydroxyl group with acid chloride or anhydride, for example, acetate, propionate, benzoate and the like.

The term "hydroxy-protecting reagent" as used herein refers to those reagents which react with the hydroxy functionality to give the hydroxy protected groups described above. For example, the hydroxy-protecting reagent acetic anhydride affords the acetyl hydroxy-protecting group. These reagents are described in Greene, "Protective Groups In Organic Synthesis," (John Wiley & Sons, New York (1981)).

The term "alkylating reagent" refers to a reagent capable of placing an alkyl group onto a nucleophilic site, including, but not limited to, alkyl halides such as methyl bromide, ethyl bromide, n-propyl bromide, dimethyl sulfate, diethyl sulfate, and di-n-propyl sulfate, and alkyl or aryl sulfonates such as methyl-p-toluenesulfonate, ethyl methanesulfonate, n-propylmethanesulfonate, and the like.

The term "reducing reagent" refers to a reagent which reacts with a keto moiety to yield a compound with an alcohol functionality. Examples include but are not limited to sodium borohydride, lithium borohydride, potassium borohydride, tert-tetraethylammonium borohydride, n-butylammonium borohydride, and the like.

The term "silyl" refers to a group of the formula Si $(R_1)(R_2)(R_3)$, where $R_1$, $R_2$, and $R_3$ are at each occurrence triisopropyl, t-butyldimethyl, triethyl, isopropyldimethyl, t-butyldiphenyl, methyldiisopropyl, methyldi-t-butyl, tribenzyl, or triphenyl, or $R_3Si$—X, where X is a halide, including chlorine, bromine, and iodine, p-toluenesulfonate or trifluoromethanesulfonate.

Abbreviations which have been used in the descriptions of the scheme and the examples that follow are: IPA for isopropyl alcohol, TMS for trimethylsilyl; cbz for benzyloxycarbonyl; DMSO for dimethyl sulfoxide; THF for tetrahydrofuran; TIPSOTf for triisopropylsilyl trifluoromethanesulfonate; HMDS for hexamethyldisilazane; OTf for trifluoromethanesulfonate; NMP for N-methyl-2-pyrrolidone; HMPA for hexamethylphosphoric triamide; DME for 1,2 dimethoxyethane; NCS for N-chlorosuccinimide; DDQ for 2,3-dichloro-5,6-dicyano-1,4-benzoquinone; PDC for pyridinium dichromate; PCC for pyridinium chlorochromate/pyridine; and py for pyrimidine.

The process of the claimed invention relates to the preparation of 6-O-methyl erythromycin A. The process comprises protecting the 2'-hydroxyl or both the 2' and 4"-hydroxyl groups of erythromycin A and reducing the 9-ketone to a hydroxyl group. The 9-hydroxyl is protected and the protected erythromycin derivative thus obtained is methylated at the 6-position. Deprotection of the protected hydroxy groups and oxidation of the 9-hydroxyl group yields 6-O-methyl erythromycin A, as the final product.

A schematic illustration of the synthesis of a specific stereoisomer in accordance with the present invention is set forth below in Scheme 1. Contemplated equivalents of the compounds of the invention include those wherein the compound bears the same or essentially the same ring structure without regard for specific stereochemistry. Such equivalent compounds can be prepared in a conventional manner in accordance with the detailed description of the invention set forth herein.

Scheme 1

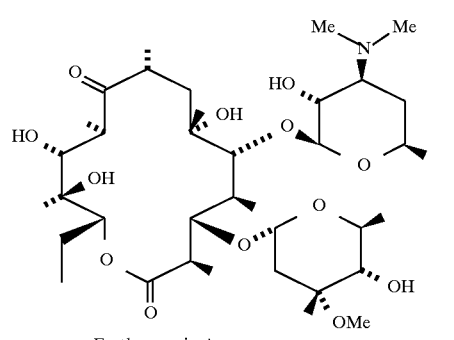

Erythromycin A
(1)

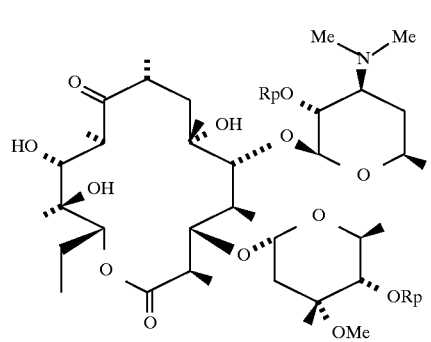

(2)

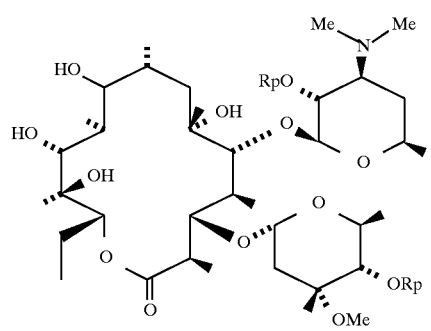

(3)

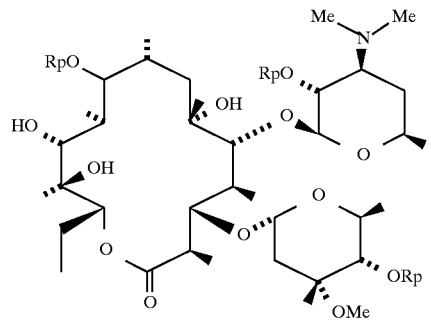

(4)

-continued
Scheme 1

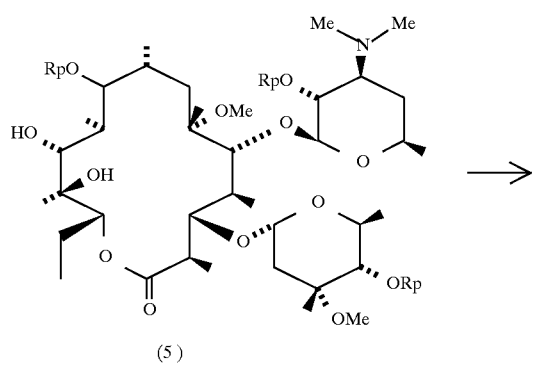

(5)

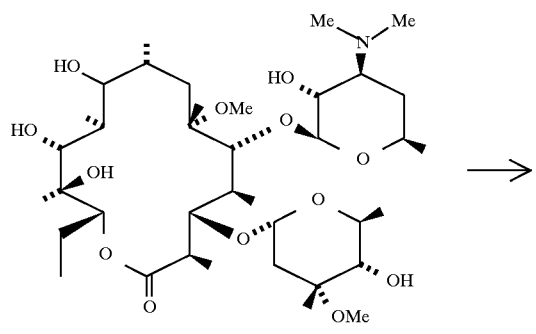

(6)

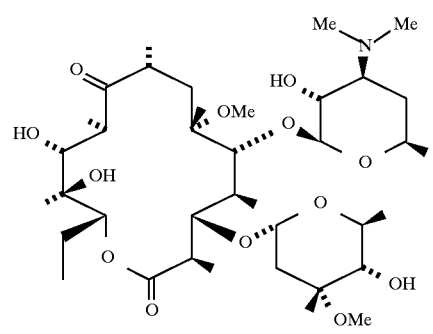

6-O-Methyl Erythromycin A
(7)

In accordance with Scheme 1, the erythromycin A starting material, Compound (1), is protected with a hydroxy protecting group to form Compound (2), a protected erythromycin A derivative wherein $R_p$ is independently hydrogen or a hydroxy protecting at each occurrence. In the preferred embodiment, both the 2'- and the 4"-hydroxyl groups are protected and $R_p$ at each occurrence is a hydroxy protecting group. Protection of both moieties is accomplished using a reagent having a silyl group. In such case, exemplary and preferred silyl groups have the formula:

wherein $R_1$, $R_2$, and $R_3$ are each independently hydrogen, lower alkyl, aryl, phenyl, phenyl substituted lower alkyl, cycloalkyl or alkenyl. Preferably, all of $R_1$, $R_2$, and $R_3$ are methyl. Silyl groups can be positioned at the 2'- and 4"-positions by reacting erythromycin A with HMDS in the presence of a suitable solvent, e.g. acetonitrile. Other trimethylsilyl reagents are also suitable for protection of both the 2'- and 4"-hydroxyl functionalities, including for example: trimethylsilyl chloride in the presence of triethylamine, pyridine, imidazole, or di-trimethylsilyl amine; hexamethyldisiloxane/ethylamino-p-toluenesulfonate; N,O-bis(trimethylsilyl)acetamide/DMF; ethyl(trimethylsilyl) acetate/n-butylammonium fluoride; trimethylsilyl-N-trimethylsilyl carbamate; and trimethylsilyl-N-trimethylsilyl sulfamide.

In another embodiment, it is only necessary to protect the 2'-hydroxyl group and $R_p$ at the 2' position of Compound (2) is a hydroxy protecting group while at the 4" position $R_p$ is hydrogen. The 2'-protected embodiment is described in U.S. patent application Ser. No. 08/627,795, filed Apr. 2, 1996, incorporated herein by reference. Conventional O-protecting groups commonly known in the art are used to protect only the 2'-hydroxyl group. Suitable O-protecting groups are reacted with the erythromycin A in the presence of a base and a solvent. Suitable bases are organic bases such as triethylamine, pyridine, and diethylamine. An exemplary and preferred solvent is an organic solvent, such as methylene chloride. Exemplary and preferred protecting groups are described in Green and Wuts' *Protective Groups in Organic Synthesis*, 2d. Ed. John Wiley & Sons, Inc., New York, 1991, the disclosure of which is incorporated herein by reference.

Conventional protecting groups, as set forth above, are positioned using standard procedures well known in the art. By way of an example, an acetyl group can be positioned at the 2'-position by reacting erythromycin A with an acetylating reagent and a base. Presence of the base is not essential to the protection of the hydroxyl group. When base is used, suitable bases include but are not limited to organic bases such as triethylamine, pyridine, diethylamine, and the like. Suitable protecting groups include but are not limited to compounds having the formula —O—C(O)$_n$—R wherein n is 0, 1, 2, and R is an alkyl, substituted alkyl, alkoxy, substituted alkoxy, alkoxyalkyl, aryl, or substituted aryl group. In particular, preferred protecting groups include anhydride and acid halide compounds of the particular formula (RCO)$_2$O or RCOCl, where R is hydrogen or a substituent group such as lower alkyl (e.g., methyl ethyl, n-propyl, isopropyl, n-butyl, sec-butyl, t-butyl and the like or aryl (e.g., phenyl, p-methoxyphenyl, p-chlorophenyl, m-nitrophenyl, p-nitrophenyl, benzylhydryl, 1-naphyl and the like).

Reduction of the 9-ketone group of Compound (2) forms a 9-hydroxyl erythromycin A derivative, Compound (3). Reduction of the 9-ketone to a 9-hydroxyl is accomplished using a reducing agent known in the art. Exemplary and preferred reagents include sodium borohydride, lithium borohydride, potassium borohydride, tert-tetraethylammonium borohydride, n-tetraethylbutylammonium borohydride, zinc borohydride, trimethoxy sodium borohydride, triisoproxy sodium hydroboride, tri-tert-butoxy sodium borohydride, sodium cyanate borohydride, triisopropylpotassium borohydride, triethyllithium borohydride, triethylpotassium borohydride, ethyllithium borohydride, and the like. Although borohydride reagents offer certain advantages in selectivity and control of the ketone reduction, other reagents, such as complex metal hydrides, are also suitable to reduce the secondary alcohol. By way of example, the mixture of 2'-4"-bis-OTMS erythromycin A is added to sodium borohydride at room temperature in the presence of THF. The reactive mixture is quenched with sodium carbonate solution and triethanolamine. The mixture is extracted with ethylacetate, drying the product over sodium sulfate to yield 2',4"-O-bis(trimethylsilyl)-9-hydroxyl-erythromycin A. Typically, one equivalent of the 9-keto erythromycin A derivative is reacted with 5 to 10 equivalents of a suitable reducing reagent.

Alternatively, ketone reduction is accomplished before protection of the 2'- and optional 4"-hydroxyl groups. In this case, $R_p$ of Compound (3) is hydrogen at each occurrence. Where reduction is accomplished at the outset of the claimed process, protection of the 9-hydroxyl and the 2'- and/or 4"-hydroxyl groups, is achieved in either a stepwise manner, i.e. protecting the 9-hydroxyl and the 2'- or 2'- and 4"-hydroxyl groups using different reagents or reaction conditions, or simultaneously, ie. protecting the 9-, 2'-, and 4"-hydroxyl groups with the same reagent and under the same conditions. The order in which the 9-, 2'-, and 4"-hydroxyl groups are protected is not critical to the invention. Reagents and conditions used for the protection of the 9-, 2'-, and 4"-hydroxyl groups and the reduction of the 9-ketone are essentially the same as described above.

Protection of the 9-hydroxy group of Compound (3) yields Compound (4), an erythromycin A derivative wherein $R_p$ is a hydroxy protecting group at the 9- and 2'-position, and either hydrogen or a hydroxy protecting group at the 4"-position. Protection of the 9-hydroxyl group is achieved in a manner similar to the protection of the 2'- and optionally the 4"-hydroxyl groups. Preferably, the 9-hydroxyl protection is accomplished using a silyl group. By way of example, the 9-hydroxyl can be protected by reacting the 9-hydroxyl with a silylating agent triisopropylsilyl trifluoromethanesulfonate (TIPSOTf) in the presence triethylamine and tetrahydrofuran (THF). Exemplary and preferred silyl groups have the formula $R_1R_2R_3SiOTf$, wherein $R_1$, $R_2$, and $R_3$ are each triisopropyl, tert-butyldimethyl, triethyl, isopropyldimethyl, t-butyldiphenyl, methyldiisopropyl, methyldi-tert-butyl, tribenzyl, and triphenyl. Preferably, all of $R_1$, $R_2$, and $R_3$ are triisopropyl. Other conditions for the transformation include reacting the 9-hydroxyl erythromycin A derivative with a reagent of the formula $R_1R_2R_3Si$—X, where X is a halide, including chloride, bromide, iodide, p-toluenesulfonate or trifluoromethanesulfonate. Such reagents are used in the presence of triethylamine, pyridine, imidazole, di-trimethylsilyl amine. In the alternative, other conventional hydroxyl protection groups, such as those used for the protection of the erythromycin 2'-hydroxyl group, are also suitable for protecting the 9-position alcohol of the 9-hydroxy erythromycin A derivative.

Methylation of Compound (4) yields Compound (5), a 6-O-methyl erythromycin A derivative. Methylation is achieved by reacting the protected derivative, Compound (4), with a methylating reagent in the presence of a suitable base. The reaction is carried out with the methylating reagent in the presence of a strong alkali metal base, stirred or agitated in a polar aprotic solvent of a mixture thereof, and maintained at a reaction temperature for a period of time sufficient to effect methylation. Preferably, the methylation reaction will be carried out at a temperature from −15° C. to room temperature for a period of 1 to 8 hours. Suitable methylating reagents include methyl iodide, methyl bromide, dimethylsulfate, methyl-p-toluenesulfonate, and the like. The amount of methylating reagent used is from 1 to 10 molar equivalents relative to the protected 9-hydroxy erythromycin derivative. The alkali metal base is selected from the group comprising sodium hydride, sodium hydroxide, potassium hydride, potassium hydroxide, and potassium butoxide. The amount of the base used is usually 1 to 10 equivalents relative to the starting compound. Exemplary and preferred solvents are polar aprotic solvents such as N,N-dimethylformamide (DMF), dimethylsulfoxide (DMSO), N-methyl-2-pyrrolidone (NMP), hexamethylphosphorictriamide (HMPA), tetrahydrofuran (THF), 1,2-dimethoxyethane (DME), acetonitrile methyl-t-butyl or ethyl acetate, or a mixture of such polar aprotic solvents.

The preparation of 6-O-methyl erythromycin A proceeds by removing the O-protecting silyl groups from the 2'-position and the 4"-position, if protected, as well as the 9-position of the erythromycin derivative Compound (5) to afford Compound (6). Means for removing the O-protecting groups are well known in the art. In one preferred method, the 2',4"-bis-OTMS-9-triisopropylsilyloxy-6-O-methyl erythromycin A can be reacted with tetrabutylammonium fluoride in THF. Other exemplary and preferred means of removing the silyl groups include but are not limited to (a) acetyl alcohol/THF/water, (b) citric acid/methanol, (c) Dowex resin/methanol, (d) n-butylammonium chloride/potassium fluoride or (d) hydrogen fluoride/acetonitrile. The protecting groups can be removed simultaneously as described above or in a multi-stage manner using a weak acid, such as formic acid, acetic acid and the like, in the presence of a hydroxylic solvent, such as methanol.

Oxidation of the hydroxyl group at the 9-position of Compound (6) yields the 6-O-methyl erythromycin A product, Compound (7). The oxidation is carried out under typical conditions suitable for oxidizing the secondary alcohol functional group. The oxidation methods include but are not limited to: (a) TPAP oxidation, (b) Swern oxidation, (c) methyl sulfide, N-chlorosuccinimide/TEA, (d) DMSO, acetyl acetate, (e) DMSO, thionyl chloride/TEA, (f) DMSO, oxalyl chloride/TEA, (g) DMSO, methanesulfonic anhydride/fEA, (h) DDQ, (i) PDC, (j) PCC, py, (k) chromate-polymer, (l) chromate.2py, and (m) Dess Martin oxidation. By way of an example, Dess Martin reagent is added to a solution of 9-hydroxy-6-O-methyl erythromycin A in dichloromethane at ambient temperature and quenched with a saturated sodium carbonate solution followed by sodium disulfite solution. The aqueous layer is extracted with dichoromethane and the organic layers are dried over sodium sulfate. Once the product is evaporated to dryness the final product 6-O-methyl erythromycin is collected.

In another aspect, the present invention provides certain intermediates formed during a process of this invention. Such intermediates correspond to the structure below,

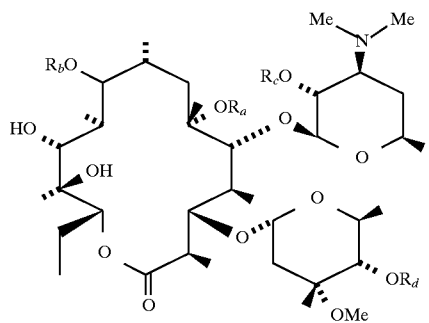

wherein $R_a$ is hydrogen or methyl; $R_b$, $R_c$, and $R_d$ are a hydrogen or a hydroxy protecting group. The hydroxy protecting group is selected from the group consisting of a group of the formula:

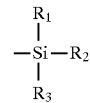

wherein $R_1$, $R_2$, and $R_3$ are independently at each occurrence triisopropyl, t-butyldimethyl, triethyl, isopropyldimethyl, t-butyldiphenyl, methyldiisopropyl, methyldi-t-butyl, tribenzyl, and triphenyl; $R_3Si$—X, where X is a halide including chlorine, bromine, and iodine, p-toluenesulfonate or trifluoromethanesulfonate; —O—C(O)$_n$—R where n is 0, 1, 2, and R is an alkyl, substituted allyl, alkoxy, substituted alkoxy, alkoxyalkyl, aryl, or substituted aryl; and $R_1R_2R_3SiOTf$, where $R_1$, $R_2$, and $R_3$ are as described above, with the proviso that $R_b$ is not hydrogen when $R_a$ is methyl, and $R_c$ and $R_d$ are hydrogen.

The following Examples illustrate preferred embodiments of the present invention and are not limiting of the specification and claims in any way.

Example 1

Synthesis of 2', 4"-O-Bis(trimethylsilyl)-Erythromycin A (2)

To a suspension of erythromycin A (73 g, 99.5 mmol) in acetonitrile (400 ml) was added HMDS (48 g, 297 mmol) at ambient temperature. After stirring for 30 minutes, a clear solution was formed. The solution was further stirred for 20 hours at room temperature. The product was precipitated our from the solution results. The product was filtered, washed with acetonitrile (50 ml) and dried in vacuum oven at 40° C. for 24 hours to yield 45.93 g of 2', 4"-O-bis(trimethylsilyl)-erythromycin A (2) as a white solid. $^1$Hnmr (500 MHz, CDCl$_3$): δ 2.80(1H, C2C$\underline{H}$), 1.15(3H, C2C$\underline{H}_3$), 4.14(1H, C3C$\underline{H}$), 1.89(1H, C4C$\underline{H}$), 1.08(3H, C4C$\underline{H}_3$), 3.55(1H, C5C $\underline{H}$), 1.43(3H, C6C$\underline{H}_3$), 1.66, 1.87(2H, C7C$\underline{H}_2$), 2.73(1H, C8C$\underline{H}$), 1.17(3H, C8C$\underline{H}_3$), 3.09(1H, C10C$\underline{H}$), 1.14(3H, C10C$\underline{H}_3$), 3.84(1H, C11C$\underline{H}$), 3.87(1H, C11O$\underline{H}$), 1.15(3H, C12C$\underline{H}_3$), 3.06(1H, C12O$\underline{H}$), 4.99(1H, C13C$\underline{H}$), 1.91, 1.49 (2H, C14C$\underline{H}_2$), 0.89(3H, C15C$\underline{H}_3$), 4.38(1H, C1'C$\underline{H}$), 3.16 (1H, C2'C$\underline{H}$), 0.10(9H, C2'O—Si—(C$\underline{H}_3$)$_3$), 2.53(1H, C3'C $\underline{H}$), 2.22(6H, C3'N—(C$\underline{H}_3$)$_2$), 1.65, 1.16(2H, C4'C$\underline{H}_2$), 3.59 (1H, C5'C$\underline{H}$), 1.15(3H, C6'C$\underline{H}_3$), 4.84(1H, C1"C$\underline{H}$), 2.36, 1.49(2H, C2"C$\underline{H}_2$), 1.15(3H, C3"C$\underline{H}_3$), 3.30(3H, C3"OC $\underline{H}_3$), 3.14(1H, C4"C$\underline{H}$), 0.14(9H, C4"O—Si—(C$\underline{H}_3$)$_3$), 4.21 (1H, C5"C$\underline{H}$), 1.19(3H, C6"C$\underline{H}_3$). $^{13}$Cnmr (125 MHz, CDCl$_3$): δ 176.5(C=O), 44.8(C2), 15.5(C2$\underline{C}$H$_3$), 79.5(C3), 40.5(C4), 9.6(C4$\underline{C}$H$_3$), 81.5(C5), 75.3(C6), 27.3(C6$\underline{C}$H$_3$), 39.0(C7), 44.4(C8), 18.3(C8$\underline{C}$H$_3$), 221.1(C9C=O), 38.6 (C10), 11.8(C10$\underline{C}$H$_3$), 68.9(C11), 74.9(C12), 16.3(C12 $\underline{C}$H$_3$), 77.0(C13), 21.3(C14), 10.8(C15$\underline{C}$H$_3$), 102.8(C1'), 73.2(C2'), 1.0(C2'O—Si—(C$\underline{H}_3$)$_3$), 65.1(C3'), 40.9 (C3'N—(C$\underline{H}_3$)$_2$), 29.7(C4'), 67.8(C5'), 21.6(C6'), 96.7(C1"), 35.8(C2"), 73.1(C3"), 22.1 (C3"$\underline{C}$H$_3$), 49.7(C3"O$\underline{C}$H$_3$), 80.9 (C4"), 0.9(C4"O—Si—(C$\underline{H}_3$)$_3$), 65.0(C5"), 19.3(C6"$\underline{C}$H$_3$).

MS (m/z): ESI 878[m+H]$^+$.

EXAMPLE 2

Synthesis of 2',4"-O-Bis(trimethylsilyl)-9-Hydroxyl-Erythromycin A (3)

To a mixture of 2',4"-O-bis(trimethylsilyl)-erythromycin A (2) (15 g, 17.7 mmol) in absolute ethanol (176 ml) was added sodium borohydride (776 mg, 20.5 mmol) at room temperature. The resulting reaction mixture was stirred at ambient temperature for 3 hours. The reaction was quenched with 5% NaHCO$_3$ solution (132 ml), triethanolamine (15 g) was then added. The resulting mixture was stirred at for 30 minutes. The product was extracted with ethylacetate (3×400 ml). The combined organic layers were washed with brine, dried over Na$_2$SO$_4$ and evaporated to dryness to yield 15.84 g of 2',4"-O-Bis(trimethylsilyl)-9-hydroxylerythromycin A (3) as a white foam. MS(ESI): m/z 880 (m+H). $^1$Hnmr (500 MHz, CDCl$_3$): δ 2.71(1H, C2CH), 1.19(3H, C2CH$_3$), 4.33(1H, C3CH), 1.83(1H, C4CH), 1.09 (3H, C4CH$_3$), 3.67(1H, C5CH), 1.27(3H, C6CH$_3$), 1.65, 1.28(2H, C7CH$_2$), 2.16(1H, C8CH), 1.11(3H, C8CH$_3$), 3.33 (1H, C9CH), 1.98(1H, C10CH), 1.17(3H, C10CH$_3$), 3.73 (1H, C11CH), 4.17(1H, C11OH), 1.12(3H, C12CH$_3$), 2.80 (1H, C12OH), 4.86(1H, C13CH), 1.94, 1.49(2H, C14CH$_2$), 0.90(3H, C15CH$_3$), 4.56(1H, C1'CH), 3.20(1H, C2'CH), 0.09(9H, C2'O—Si—(CH$_3$)$_3$), 2.55(1H, C3'CH), 2.24 (6H, C3'N—(CH$_3$)$_2$), 1.64, 1.19(2H, C4'CH$_2$), 3.70(1H, C5'CH$_3$), 1.16(3H, C6'CH$_3$), 4.96(1H, C1"CH), 2.41, 1.50 (2H, C2"CH$_2$), 1.15(3H, C3"CH$_3$), 3.31(3H, C3"OCH$_3$), 3.17(1H, C4"CH), 0.14(9H, C4"O—Si—(CH$_3$)$_3$), 4.23(1H, C5"CH), 1.24(3H, C6"CH$_3$). $^{13}$Cnmr (125 MHz, CDCl$_3$): δ 177.6(C=O), 44.6(C2), 14.0(C2CH$_3$), 78.7(C3), 43.0(C4), 10.0(C4CH$_3$), 81.0(C5), 75.1(C6), 26.3(C6CH$_3$), 36.9(C7), 34.4(C8), 19.8(C8CH$_3$), 83.2(C9), 32.3(C10), 14.8(C10CH$_3$), 70.5(C11), 75.1(C12), 16.4(C12CH$_3$), 77.3(C13), 21.8(C14), 11.3(C15CH$_3$), 102.3(C1'), 73.1(C2'), 0.90 (C2'O—Si—(CH$_3$)$_3$), 65.1(C3'), 40.9(C3'N—(CH$_3$)$_2$), 29.8 (C4'), 68.1(C5'), 21.4(C6'), 96.6(C1"), 35.4(C2"), 73.0 (C3"), 22.3(C3"CH$_3$), 49.4(C3"OCH$_3$), 80.7(C4"), 0.80 (C4"O—Si—(CH$_3$)$_3$), 65.4(C5"), 19.1(C6"CH$_3$).

MS (m/z): ESI 880[m+H]$^+$.

EXAMPLE 3

Synthesis of 2',4"-O-Bis(trimethylsilyl)-9-Triisopropylsilyloxy-Erythromycin A (4)

To a solution of 2',4"-O-bis(trimethylsilyl)-9-hydroxylerythromycin A (3) (7.0 g, 7.95 mmol) in dichloromethane (48 ml) was added triethylamine (2.4 ml, 17.5 mmol) and triisopropylsilyl trifluoromethanesulfonate (4.3 ml, 15.9 mmol). The resulting reaction mixture was stirred at ambient temperature overnight and refluxed for 3 hours before cooling back to ambient temperature. The reaction mixture was then quenching with 5% NaHCO$_3$ (20 ml). Organic layer was separated, dried over Na$_2$SO$_4$, filtered and concentrated to yield 10.1 g of orange foam. The resulting crude material was further purified by flash silica gel column chromatography. Elution with 15% acetone/hexane mixture gave fractions of desired product which were combined and concentrated to dryness to yield yellowish white foam. Titration with acetone (25 ml) followed by filtration of the product yielded 3.75 g of 2',4"-O-bis(trimethylsilyl)-9-triisopropylsilyloxy -erythromycin A (4) as a white powder. MS(ESI): m/z 1035 (m+H). $^1$Hnmr (500 MHz, CDCl$_3$): δ 2.64(1H, C2CH), 1.18(3H, C2CH$_3$), 3.94(1H, C3CH), 1.74 (1H, C4CH), 1.06(3H, C4CH$_3$), 3.50(1H, C5CH), 1.19(3H, C6CH$_3$), 1.81, 1.13(2H, C7CH$_2$), 2.36(1H, C8CH), 1.07 (3H, C8CH$_3$), 3.67(1H, C9CH), 1.19(3H, C9O—Si—(CH)$_3$), 1.13, 1.12(18H, C9O—Si—C—(CH$_3$)$_6$), 2.00(1H, C10CH), 1.19(3H, C10CH$_3$), 3.85(1H, C11CH), 4.02(1H, C11OH), 1.12(3H, C12CH$_3$), 4.93(1H, C13CH), 1.93, 1.46 (2H, C14CH$_2$), 0.92(3H, C15CH$_3$), 4.70(1H, C1'CH), 3.21 (1H, C2'CH), 0.08(9H, C2'O—Si—(CH$_3$)$_3$), 2.56(1H, C3'CH), 2.21(6H, C3'N—(CH$_3$)$_2$), 1.63, 1.17(2H, C4'CH$_2$), 3.74 (1H, C5'CH), 1.15(3H, C6'CH$_3$), 4.99(1H, C1"CH), 2.39, 1.47(2H, C2"CH$_2$), 1.14(3H, C3"CH$_3$), 3.32(3H, C3"OCH$_3$), 3.15(1H, C4"CH), 0.13(9H, C4"O—Si—(CH$_3$)$_3$), 4.14 (1H, C5"CH), 1.17(3H, C6"CH$_3$). $^{13}$Cnmr (125 MHz, CDCl$_3$): δ 176.8(C=O), 44.9(C2), 13.4(C2CH$_3$), 78.3(C3), 44.2(C4), 10.2(C4CH$_3$), 83.7(C5), 74.1(C6), 23.3(C6CH$_3$), 38.2(C7), 35.6(C8), 19.7(C8CH$_3$), 86.6(C9), 13.0 (C9O—Si—(CH)$_3$), 18.5, 18.3(C9O—Si—C—(CH$_3$)$_6$), 32.6(C10), 15.6(C10CH$_3$), 70.4(C11), 75.2(C12), 16.5(C12CH$_3$), 77.2(C13), 22.3(C14), 11.5(C15CH$_3$), 101.4(C1'), 72.9(C2'), 0.90(C2'O—Si—(CH$_3$)$_3$), 64.9(C3'), 40.9 (C3'N—(CH$_3$)$_2$), 29.2(C4'), 67.8(C5'), 21.3(C6'), 95.6(C1"), 35.2(C2"), 73.0(C3"), 22.5(C3"CH$_3$), 49.1(C3"OCH$_3$), 80.7 (C4"), 0.80(C4"O—Si—(CH$_3$)$_3$), 65.2(C5"), 19.0(C6"CH$_3$).

MS (m/z): APCI 1037[m+H]$^+$

EXAMPLE 4

Synthesis of 2',4"-O-Bis(trimethylsilyl)-9-Triisopropylsilyloxy-6-O-Methyl Erythromycin A (5)

To a solution of 2',4"-O-bis(trimethylsilyl)-9-triisopropylsilyloxy-erythromycin A (4) (1.0 g, 0.97 mmol) in DMSO/THF (1:1, 10 ml) was added methyliodide (0.6 ml, 2.17 mmol) followed by NaH (95%, 37 mg, 1.45 mmol). The resulting mixture was stirred for 4 hours maintaining the temperature at 5° to 10° C. and quenched with 50% brine solution (10 ml). The methylation product was extracted with hexane (2×25 ml). The combined organic layers were dried over Na$_2$SO$_4$ and evaporated to dryness to yield white solid (950 mg) as a crude material. Desired product was purified via flash silica gel column chromatography. Product was eluted with 10% acetone/hexane/0.2% triethylamine mixture. Desired fractions were collected and evaporated to dryness to obtain 190 mg of 2',4"-O-bis(trimethylsilyl)-9-triisopropylsilyloxy-6-O-methyl erythromycin A (5) as a white solid. MS(ESI): m/z 1051 (m+H).

EXAMPLE 5

Synthesis of 9-Hydroxy-6-O-Methyl Erythromycin A (6)

To a solution of 2',4"-O-bis(trimethylsilyl)-9-triisopropylsilyloxy-6-O-methyl erythromycin A (5) (420 mg, 0.34 mmol) in THF (4.2 ml) was added tetrabutylammonium fluoride (1M, 1.9 ml). The reaction mixture was stirred at ambient temperature for 1.5 hours. After addition of H$_2$O (10 ml), THF was evaporated. Product was extracted with isopropyl acetate (2×10 ml), the combined organic layers were dried over Na$_2$SO$_4$ and concentrated to dryness to yield 300 mg of 9-hydroxy-6-O-methyl erythromycin A (6) as a white solid. MS(ESI): m/z 750 (m+H). $^1$Hnmr (500 MHz, CDCl$_3$): δ 2.97(1H, C2CH), 1.23(3H, C2CH$_3$), 3.73 (1H, C3CH), 2.01(1H, C4CH), 1.13(3H, C4CH$_3$), 3.82(1H, C5CH), 1.39(3H, C6CH$_3$), 3.37(3H, C6OCH$_3$), 1.61, 1.48 (2H, C7CH$_2$), 2.14(1H, C8CH), 0.92(3H, C8CH$_3$), 3.29(1H, C9CH), 5.72(1H, C9OH), 1.86(1H, C10CH), 1.11(3H, C10CH$_3$), 3.53(1H, C11CH), 4.34(1H, C11OH), 1.09(3H, C12CH$_3$), 3.01(1H, C12OH), 5.20(1H, C13CH), 1.94, 1.49 (2H, C14CH$_2$), 0.84(3H, C15CH$_3$), 4.49(1H, C1'CH), 3.19 (1H, C2'CH), 2.43(1H, C3'CH), 2.30(6H, C3'N—(CH$_3$)$_2$), 1.66, 1.21(2H, C4'CH$_2$), 3.51(1H, C5'CH), 1.23(3H, C6'CH$_3$), 4.98(1H, C1"CH), 2.38, 1.61(2H, C2"CH$_2$), 1.26(3H, C3"CH$_3$), 3.34(3H, C3"OCH$_3$), 3.03(1H, C4"CH), 2.21(1H, C4"OH), 4.05(1H, C5"CH), 1.31(3H, C6"CH$_3$). $^{13}$Cnmr (125 MHz, CDCl$_3$): δ 175.2(C=O), 45.3(C2), 16.3(C2CH$_3$), 79.0(C3), 38.5(C4), 9.30(C4CH$_3$), 78.4(C5), 80.3

(C6), 20.5(C6CH₃), 50.8(C6OCH₃), 34.6(C7), 34.7(C8), 21.4(C8CH₃), 82.0(C9), 32.5(C10), 16.8(C10CH₃), 70.9 (C11), 74.9(C12), 16.4(C12CH₃), 77.2(C13), 21.3(C14), 10.6(C15CH₃), 102.5(C1'), 71.0(C2'), 65.5(C3'), 40.2 (C3'N—(CH₃)₂), 28.6(C4'), 68.6(C5'), 21.5(C6'), 96.5(C1"), 35.0(C2"), 72.6(C3"), 21.5(C3"CH₃), 49.5(C3"OCH₃), 77.9 (C4"), 65.9(C5"), 18.7(C6"CH₃).

MS (m/z): ESI 750[m+H]

EXAMPLE 6

6-O-Methyl Erythromycin A (7)

To a solution of 9-hydroxy-6-O-methyl erythromycin A (6) (150 mg, 0.2 mmol) in dichloromethane (6 ml) added Dess-Martin reagent (85 mg, 0.4 mmol). The resulting reaction mixture was stirred at ambient temperature under N₂ for about 7 hours. Reaction mixture was quenched with saturated NaHCO₃ solution (10 ml) followed by addition of Na₂S₂O₅ (80 mg). The mixture was stirred for 30 minutes. The organic layer was separated and the aqueous layer was extracted with dichloromethane (2×10 ml). The combined organic layers were dried over Na₂SO₄, filtered and evaporated to dryness to yield 130 mg of 6-O-methyl erythromycin A (7) as a white solid. MS(ESI): m/z 748 (m+H).

What is claimed is:

1. A process for the preparation of 6-O-methyl erythromycin A comprising:
   a.) protecting the 2' hydroxyl group of erythromycin A to form a 2' protected erythromycin A derivative;
   b.) reducing the 9-keto group of the 2' protected erythromycin A derivative to form a 9-hydroxy-2'-protected erythromycin A derivative;
   c.) protecting the 9-hydroxy 2'-protected erythromycin A to form a 9-protected 2'-protected erythromycin A derivative;
   d.) methylating the 6-position of the 9-protected-2'-protected erythromycin A derivative to form a 9-protected-2'-protected 6-O-methyl erythromycin A derivative;
   e.) deprotecting the 9-protected-2'-protected 6-O-methyl erythromycin A derivative to form a 9-hydroxy 6-O-methylated erythromycin A derivative; and
   f.) oxidizing the 9-hydroxy of the 9-hydroxy 6-O-methylated erythromycin A to form 6-O-methyl erythromycin A.

2. The process according to claim 1 wherein the reducing reagent is a borohydride reagent.

3. The process according to claim 1 wherein the methylating reagent is Me—X, where X is a halide, or Me—R₄, where R₄ is a sulfate or a p-toluenesulfonate.

4. The process according to claim 1 wherein the oxidizing reagent is Dess Martin reagent.

5. The process according to claim 1 further comprising the step of protecting the 4" hydroxyl group of erythromycin A.

6. The process according to claim 1, wherein the erythromycin A is treated with a hydroxyl protecting reagent selected from the group consisting of:
   (a) R₁R₂R₃Si—X, wherein R₁, R₂, R₃ are each independently selected from the group consisting of hydrogen, lower alkyl, aryl, phenyl substituted lower alkyl, cycloalkyl, and alkenyl, and where X is selected from the group consisting of halide, chlorine, bromine, iodine, p-toluenesulfonate; and trifluoromethanesulfonate;
   (b) Y—C(O)—R—Z, wherein Y is hydroxy or halide; R is alkyl, substituted alkyl, aryl, or substituted aryl, and Z is hydrogen or a group of the formula —C(O)OR', wherein R' is selected from the group as defined for R above;
   (c) (R₄CO)₂O, wherein R₄ is selected from the group as defined for R above; and
   (d) R₁R₂R₃SiOTf, wherein R₁, R₂, R₃ are as defined in (a) above.

7. The process according to claim 1 wherein the hydroxy protecting reagent is selected from the group consisting of trimethylsilyl chloride, hexamethyldisiloxane, N,O-bis(trimethylsilyl)acetamide, ethyl(trimethylsilyl acetate), trimethylsilyl-N-trimethylsilyl carbamate, and trimethylsilyl-N-trimethylsilyl sulfamide.

8. A compound having the formula:

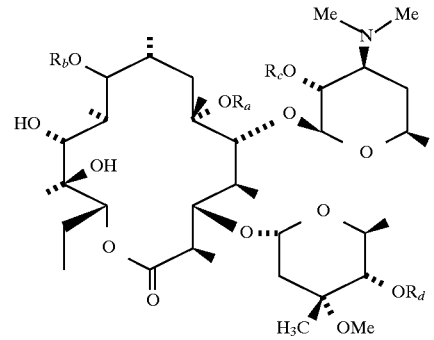

wherein:
   R_a is hydrogen or methyl;
   R_b, R_c, and R_d are independently at each occurrence a hydrogen or a hydroxy protecting group selected from the group consisting of the formula:

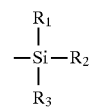

wherein R₁, R₂, and R3 are each independently selected from the group consisting of hydrogen, lower alkyl, aryl, phenyl, phenyl substituted lower alkyl, cycloalkyl, and alkenyl; and —C(O)ₙ—R where n is 0, 1, 2, and R is an alkyl, substituted alkyl, alkoxy, substituted alkoxy, alkoxyalkyl, aryl, or substituted aryl, with the proviso that R_b is not hydrogen when R_a is methyl, and R_c and R_d are hydrogen.

9. A compound according to claim 8, wherein R_a is hydrogen, R_b, R_c, and R_d are hydroxy protecting groups.

10. A compound according to claim 8, wherein R_a, R_d are hydrogen, R_b and R_c are hydroxy protecting groups.

11. A compound according to claim 8, wherein R_a is methyl, R_b, R_c, and R_d are hydroxy protecting groups.

12. A compound according to claim 8, wherein R_a is methyl, R_b, R_c are hydroxy protecting groups, and R_d is hydrogen.

13. A compound according to claim 8, wherein R_a, R_b are hydrogen, R_c and R_d are hydroxy protecting groups.

14. A compound according to claim 8, wherein R_a, R_b, R_d are hydrogen, and R_c is a hydroxy protecting group.

* * * * *

UNITED STATES PATENT AND TRADEMARK OFFICE
CERTIFICATE OF CORRECTION

PATENT NO. : 5,892,008
DATED : Apr. 6, 1999
INVENTOR(S) : Ku et al.

It is certified that error appears in the above-identified patent and that said Letters Patent is hereby corrected as shown below:

On the title page: Item
    [75], change "Buffalo. Ill." to --Buffalo Grove, Ill.--.

Signed and Sealed this

Twenty-ninth Day of February, 2000

Attest:

Q. TODD DICKINSON

Attesting Officer      Commissioner of Patents and Trademarks